US010932713B2

(12) United States Patent
Lewis et al.

(10) Patent No.: US 10,932,713 B2
(45) Date of Patent: Mar. 2, 2021

(54) MOBILE MONITORING OF FRACTURE HEALING IN EXTERNAL FIXATORS

(71) Applicant: The Penn State Research Foundation, University Park, PA (US)

(72) Inventors: Gregory S. Lewis, University Park, PA (US); J. Spence Reid, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 402 days.

(21) Appl. No.: 15/873,651

(22) Filed: Jan. 17, 2018

(65) Prior Publication Data

US 2018/0214073 A1 Aug. 2, 2018

Related U.S. Application Data

(63) Continuation of application No. PCT/US2016/045358, filed on Aug. 3, 2016.
(Continued)

(51) Int. Cl.
*A61B 5/00* (2006.01)
*A61B 17/62* (2006.01)
(Continued)

(52) U.S. Cl.
CPC .......... *A61B 5/4504* (2013.01); *A61B 5/1038* (2013.01); *A61B 5/1075* (2013.01);
(Continued)

(58) Field of Classification Search
CPC ......... A61B 5/103; A61B 17/60; A61B 17/62; A61B 2562/0261; A61F 5/01
See application file for complete search history.

(56) References Cited

U.S. PATENT DOCUMENTS 3,938,379 A * 2/1976 Bingham ............ A61B 5/1107
  73/862.633
4,576,158 A * 3/1986 Boland ................ A61B 17/60
  606/102

(Continued)

FOREIGN PATENT DOCUMENTS

CN 102788068 A 11/2012
RU 2277391 C1 6/2006

OTHER PUBLICATIONS

Designation: A582/A582M—12E1, Oct. 2012, ASTM International, Oct. 2012 update, p. 1-3. (Year: 2012).*
(Continued)

*Primary Examiner* — Daniel L Cerioni
*Assistant Examiner* — Raymond P Dulman
(74) *Attorney, Agent, or Firm* — McKee, Voorhees & Sease, PLC (57) ABSTRACT

A device for and a method of monitoring the healing status of a fractured bone in a person's limb is disclosed. The external fixation device may include one or more rods or struts that incorporate strain gauges designed to measure the mechanical forces on the strut when force is applied to the fractured bone. The mechanical force data may be collected by an electronic module and transmitted to a computer for statistical analysis. The device may also include a foot insole sensor for measuring the foot plantar force to normalize the data collected by an external fixation device attached to a person's leg. The method of measuring the healing status of a fractured bone includes measuring the changes in mechanical forces exerted on the one or more struts, and based on the measurements, estimating the healing status of the bone.

9 Claims, 8 Drawing Sheets

Related U.S. Application Data (60) Provisional application No. 62/200,919, filed on Aug. 4, 2015.

(51) Int. Cl.
  *A61B 5/103*  (2006.01)
  *A61F 5/01*  (2006.01)
  *A61B 17/60*  (2006.01)
  *A61B 5/107*  (2006.01)

(52) U.S. Cl.
  CPC .......... *A61B 5/4842* (2013.01); *A61B 5/4848* (2013.01); *A61B 17/60* (2013.01); *A61B 17/62* (2013.01); *A61F 5/01* (2013.01); *A61B 2562/0261* (2013.01)

(56) References Cited

U.S. PATENT DOCUMENTS

| | | | |
|---|---|---|---|
| 5,897,555 A | 4/1999 | Clybum et al. | |
| 6,515,593 B1* | 2/2003 | Stark | A61B 5/411 128/903 |
| 7,658,739 B2 | 2/2010 | Shluzas | |
| 2006/0070260 A1* | 4/2006 | Cavanagh | A61B 5/1036 36/44 |
| 2008/0039756 A1* | 2/2008 | Thorsteinsson | A61B 5/4585 602/23 |
| 2008/0221571 A1* | 9/2008 | Daluiski | A61B 17/6466 606/54 |
| 2010/0087819 A1 | 4/2010 | Mullaney | |
| 2011/0264009 A1* | 10/2011 | Walter | A61F 2/4657 600/595 |
| 2015/0088043 A1* | 3/2015 | Goldfield | A61F 5/01 602/6 |
| 2017/0196499 A1* | 7/2017 | Hunter | A61B 5/066 |
| 2019/0336171 A1* | 11/2019 | Lavi | A61B 17/66 |

OTHER PUBLICATIONS

Razak, et al., "Foot Plantar Pressure Measurement System: A Review", Sensors Journal, vol. 12, pp. 9884-9912 (2012).

"Technique Guide, Expert Nailing System", SYNTHES Instruments and Implants, Dec. 2013, 6 pages.

The Penn State Research Foundation, PCT/US2016/045358, filed Aug. 3, 2016, "The International Search Report and the Written Opinion of the International Searching Authority, or the Declaration", dated Oct. 26, 2016.

* cited by examiner

MOBILE MONITORING OF FRACTURE HEALING IN EXTERNAL FIXATORS

CROSS-REFERENCE TO RELATED APPLICATIONS

This application is a Continuation Application of PCT Application No. PCT/US2016/045358, filed on Aug. 3, 2016, which claims priority under 35 U.S.C. § 119 to provisional application Ser. No. 62/200,919, filed on Aug. 4, 2015, all of which are herein incorporated by reference in their entirety and for all purposes.

FIELD OF THE INVENTION

The invention relates generally to a medical device. More specifically, but not exclusively, the invention relates to a modified external fixation device for stabilizing a bone during healing.

BACKGROUND OF THE INVENTION

Bone fractures are commonly seen in orthopedic clinics and emergency rooms. Bone defects occur mostly from trauma, but can also result from resections associated with bone infections and tumors. Nonunion or malunion occurs in about 10% of these cases. In 2005 in the U.S., fractures caused 127 million bed days in 4.4 million people, and 72 million lost work days—numbers larger than corresponding numbers for heart problems, stroke and hypertension. Severe fractures in the lower limb (approximately 150,000 each year in the US) are associated with high energy trauma in both civilian and military patients, and are sometimes treated with external fixation devices, such as the Ilizarov fixator, to stabilize the bone until healing has occurred. The devices are kept on the patient for up to a year at significant cost, intrusiveness, and risk of infection. The clinician must decide when to remove the device such that adequate healing has occurred and the bone will not re-fracture, but healing rates are variable, and x-rays can be inconclusive. The clinician must also identify when a patient is starting to progress poorly and an early revision surgery is needed to prevent further complications.

Therefore, there remains a need in the art for a medical device or apparatus in the art for measuring or determining the state of bone healing. The methods, system, and/or apparatus may be used to measure the forces on the external fixator struts to determine the state of bone healing. When the limb is mechanically loaded during standing and walking, the load is transmitted down through the struts of the fixator, offloading the bone defect site. As healing progresses, the bone assumes a larger and larger share of the load, and the external fixator should experience less load. This provides the opportunity to use non-invasive sensors on the external fixator to develop indicators of fracture healing, which would be helpful to patients and clinicians.

BRIEF SUMMARY OF THE INVENTION

Therefore, it is a principle object, feature, and/or advantage of the invention to improve on and/or overcome the deficiencies in the art.

It is another object, feature, and/or advantage of the invention to provide a system or apparatus for stabilizing and/or supporting damaged and/or fractured bone.

It is yet another object, feature, and/or advantage of the invention to provide an external fixator including a frame comprising one or more rings interconnected by a plurality of strut members.

It is a further object, feature, and/or advantage of the invention to provide an external fixator with modified struts that include a smooth center section.

It is still a further object, feature, and/or advantage of the invention to provide a modified strut including one or more gauges attached to a smooth center section of the strut.

It is still yet a further object, feature, and/or advantage of the invention to provide a modified strut wherein the one or more gauges are attached to the smooth center section by an epoxy.

It is still yet a further object, feature, and/or advantage of the invention to provide a modified strut wherein the one or more gauges are attached to the smooth center section by an epoxy, an acrylic coating, and/or a silicone coating.

It is still yet a further object, feature, and/or advantage of the invention to provide a modified strut including one or more strain gauges configured to measure the mechanical strains acting on the modified strut.

It is still yet a further object, feature, and/or advantage of the invention to provide a modified strut that utilizes an electronic module that is removably attached to one or more gauges by an electrical connector and is configured to measure and record the mechanical strains acting on a modified strut.

It is still yet a further object, feature, and/or advantage of the invention to provide an electronic module configured to measure and record data from one or more gauges and transmit the data to a computer through a wired or wireless connection.

It is still yet a further object, feature, and/or advantage of the invention to provide a method of measuring the healing status of a fractured and/or damaged bone by measuring the strains acting on one or more struts of an external fixator that is attached to and/or supporting the fractured and/or damaged bone, and calculating the mechanical forces on the strut to predict the healing status of a bone.

It is still yet a further object, feature, and/or advantage of the invention to provide a method of measuring the healing status of a fractured and/or damaged bone by measuring the foot plantar forces using a foot insole device.

These and/or other objects, features, and advantages of the invention will be apparent to those skilled in the art. The invention is not to be limited to or by these objects, features and advantages. No single embodiment need provide each and every object, feature, or advantage.

Various embodiments of the invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION

The invention is generally directed towards a medical device for determining the state of bone healing through the use of non-invasive sensors on the external fixator struts to develop indicators of fracture healing, which would be helpful to patients and clinicians.

An external fixator device may be modified to include struts with sensors configured to measure mechanical forces acting on the strut. For example, the Ilizarov external fixator (Smith & Nephew), and related Taylor Spatial Frames, may be modified to include the struts with sensors. The Ilizarov external fixator (Smith & Nephew) and related Taylor Spatial Frames are orthopedic devices with a long history of use in treating severe lower limb bone fractures and bone defects. The Ilizarov forms a support scaffold and stabilizes the fracture until healing has occurred. Ilizarov fixators have been used in over a million patients worldwide, and in the US since about 1981. The device includes several rings 44 external to the skin, vertical steel rods 42 which connect these rings 44 together, and steel pins 46 that connect the rings 44 directly to bone (passing through the skin). The modification involves replacing up to four of the external vertical steel rods 42 with rods 10 of similar material and size, except modified to include strain sensors 20 adhered to a smooth rod surface 14 that enable us to measure force. The modified components are all outside the patient's body.

Figure 1:
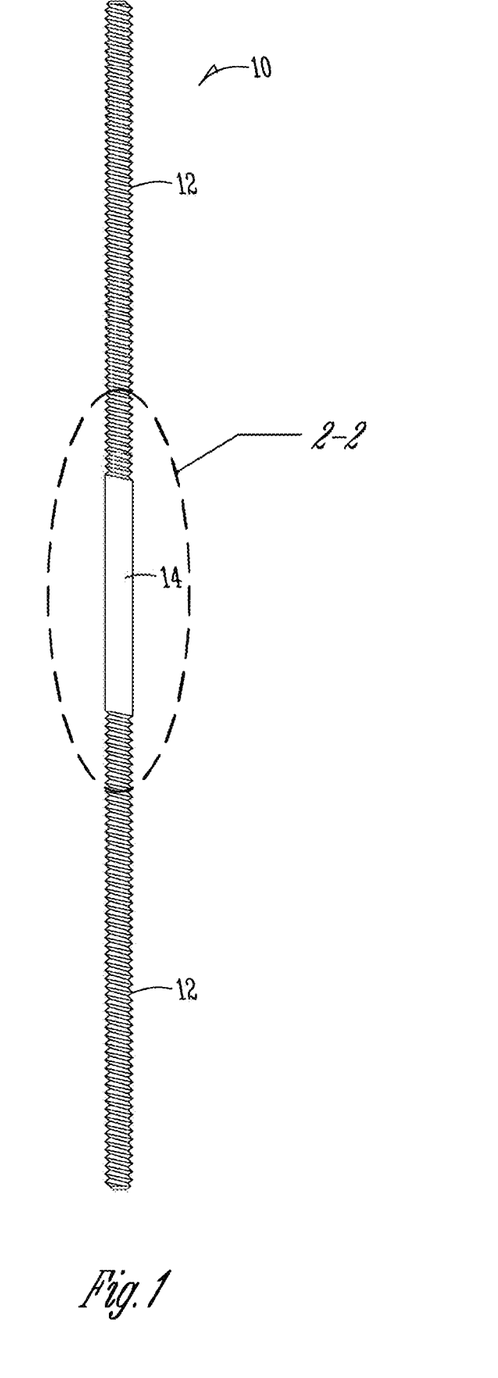
FIG. 1 is an example embodiment of a strut for an external fixator apparatus.
Figure 2:
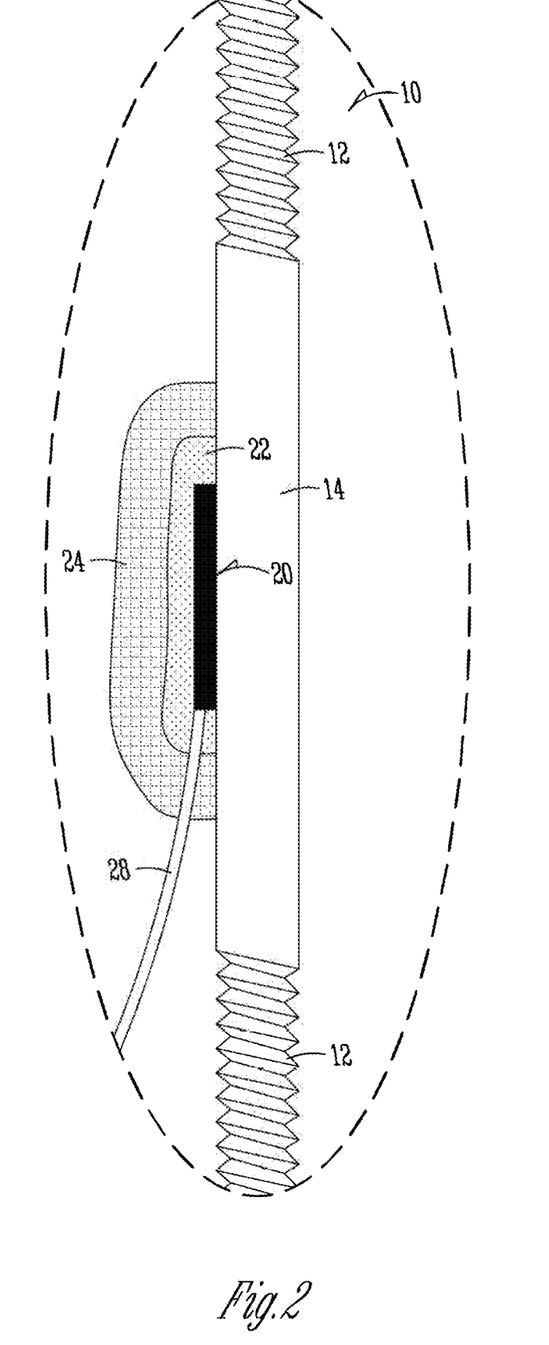
FIG. 2 is an enlarged view of the strut for an external fixator apparatus of FIG. 1, including a strain gauge assembly.
Figure 3:
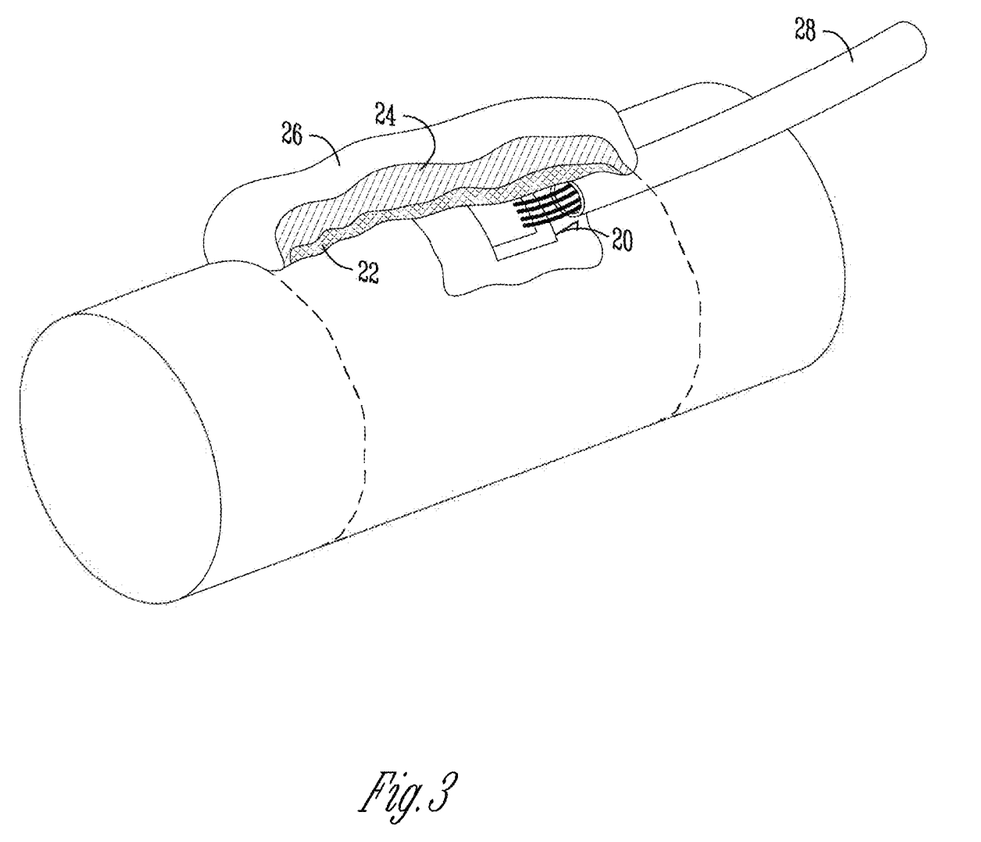
FIG. 3 is an enlarged view of the smooth central section of the strut for an external fixator apparatus of FIG. 2, including a strain gauge assembly.

The modified struts, as shown in FIG. 1, are slightly modified in design compared to the fully threaded, standard Ilizarov struts 42. The modified struts 10 may be comprised of 303 stainless steel or a similar material. The struts 10 may include one or more threaded portions 12. For example, the threaded portions 12 may be sized to M6×1. The length of the strut 10 may vary based on the length of the bone to be braced and/or the size of the fixation device. For example, the struts length may be 12 cm, 15 cm, 20 cm, and/or 25 cm. In one example embodiment, the struts 10 may be constructed from 303 SS rod stock which meets ASTM A582 and comes with certification, i.e., with a traceable lot number and material test report. The modified strut 10 includes a smooth central section 14, as shown in FIGS. 1 and 2. This section may have an approximate diameter of 6 mm and a length of approximately 38 mm (1.5 inches). The diameter of this section is similar to the major diameter of the M6×1 threads. One of the many reasons for making this smooth central surface on the struts is to accurately measure the strains (forces) with adhered strain gauges 20 (as it is impossible to achieve good contact between adhered gauges and struts if adhered to the threaded portion). Thus, the length of the smooth central section 14 was determined based on the area required for adhesion of strain gauges 20.

Struts 10 may be machined using standard documented machining and quality control protocols by an experienced machinist with documented qualifications. A final inspection and measurement of the final machined parts may be completed to ensure the final parts comply with known standards established within the industry. Gauges 20 are attached to the smooth central portion 14 of the strut 10. This region 14 is composed, as shown below in Table 1, of four strain gauges in full axial bridge, that may be attached by a thin epoxy 22 strain gauge adhesive, coated with a thin acrylic coating 24 for a water tight seal, an outer protective silicone coating 26, and a polyester mesh sleeve 32. In the preferred embodiment, the strain gauges are configured to measure pure axial loading and cancel bending effects. However, alternative strain gauge configurations, such as 1-3 uniaxial gauges, may also be used for cost considerations and/or to include bending effects. An electrical connector 28 may be attached to the gauges 20 to allow for measuring strain and other mechanical forces acting on the strut 10. The design and attachment of the gauges and wiring to the strut 10 may be done by other acceptable methods known in the art.

TABLE 1

List of materials for gauged Illizarov struts (not including the modified metal rod) - these struts are located external to the patient's skin.

| Part | Model | Size | Makeup | Purpose |
|---|---|---|---|---|
| Strain Gauges | J5E-NC-S4225-350S (Vishay) | 0.155" × 0.220" | general-purpose tee rosette in platinum-tungsten alloy | measure strains within struts |
| M-bond 610 | P-37920-00 (Vishay) | <1.5" length | 2-component, solvent-thinned, epoxy-phenolic | strain gauge adhesive |
| Gagekote #8 | P-3784-00 (Vishay) | <1.5" length | single-component, transparent, acrylic | water tight seal coating |
| Sylgard 164 | P-5855-00 (Dow Corning) | <1.5" length | 2-part, silicone, elastomer | physical protective coating |
| Shrink Tubing | NA (NA) | 1.5" length | polyolefin | outer protective layer |
| Mesh Overbraid | NA (NA) | 3" length | polyester braided mesh sleeve | protects wire & connector |
| Connector | HR582-ND (Hirose Electric) | 1.25" length Ø 0.5" | lead free, gold contacts, PPS shell | waterproof female plug leadwire connector |

TABLE 1-continued

List of materials for gauged Illizarov struts (not including the modified metal rod) - these struts are located external to the patient's skin.

| Part | Model | Size | Makeup | Purpose |
|---|---|---|---|---|
| Connector Cap | HR598-ND (Hirose Electric) | <0.125" thick Ø 0.5" | santoprene rubber | waterproof cap for connector |
| Leadwire | P-5273-00 (Belden) | 1" length | #22 AWG, Vinyl 4-cond, shielded | connects strain gauge to connector |

As noted above, the gauges 20 may be sealed with coatings for mechanical and water protection. The electrical connector 28 may include a removable attached cap 34, wherein the electrical connector 28 may be capped 34 at all times except when measurements are taken. Measurements may be taken during clinical visits. A patient may schedule a clinical visit for measurement purpose at a set interval, for example, occurring approximately once per month. The strain gauges 20 are small passive wire resistors with an insulating backing that prevents any bare wire to strut 10 contact 14. The active electronic 30, which excites the gauges 20 with a very small voltage (3V), will only be wired to the gauges 20 during the measurement sessions and removed at the end of the sessions.

The struts 42 of the Ilizarov and Taylor Spatial Frames 40 are components which are outside the patient's skin. The traditional vertical steel struts 42 utilized by the Ilizarov and/or Taylor Spatial Frames 40 were fully threaded. To incorporate the gauges 20 into the modified strut, a smooth section 14 was added to provide improved attachment of the gauges 20 to the strut 10. To ensure that the modified strut 10 would not fail, the diameter of the smooth section may be increased to provide greater mechanical properties. For example, the diameter of the smooth section 14 of the modified strut may be increased one to five millimeters. In one embodiment, the smooth section 14 of the modified strut was increased from 5-millimeters to 6-millimeters. Furthermore, if one strut were to mechanically fail, there is redundancy in the Ilizarov and/or Taylor Spatial Frames 40 structures such that the other struts 42 and 10 would carry the load.

For example, two 304 stainless steel struts 10 modified with smooth 5 mm dia. central sections 14, lengths 12 cm and 20 cm, were each cyclically tested 1 million cycles in 500 N (112 lbs) axial compression with no failure detected.

The modified struts 10 may be tested to confirm that mechanical properties of the strut 10 will support the particular application based on the location and type of fracture and/or damage to the bone to be supported. Test setup for testing the mechanical properties of a strut may include: using a servo-hydraulic mechanical testing machine. One end of the strut may be rigidly fixed to an axial load cell. After aligning the strut, cyclic loading may applied to each strut with a target peak based on the particular application of the external fixator. For example, force of 500 N may be applied to the strut 10 at a frequency of 8 Hz for 1 million loading cycles.

Summary of Clinical Study Protocol

The subject(s) or patient(s) will not perform physical tasks that are unusual for the patient population while wearing the modified external fixator device. The patient(s) will ambulate normally for a predetermined distance. For example, the patient(s) may walk down the hallway in the clinic or on a sidewalk. While the present protocol only describes the taking of measurements during routinely scheduled clinical visits, it should be understood that it is contemplated that the protocol may also include permanently mounting an electronics module onto the external fixator and log the patients data in a mobile manner during routine patient activities outside of a clinical visit.

Patient population: Patients seen by the Co-PI (Chief Ortho Trauma) at our institution for severe tibia fractures or defects that are being treated by Ilizarov external fixation.

Protocol:
As part of routine standard care the patient will receive attachment of a standard Ilizarov external fixator in a standard operation. This fixator will not be instrumented at the time of the surgery.

After consent, during a post-operative clinical visit, the gauged struts will be switched out with the normal struts, one at a time. (Changing of struts for other purposes is performed sometimes during standard clinical care.) A temporary additional strut will be added to the frame during the switching procedure. The gauged struts will be physically prepared, calibrated, and sterilized prior to the visit.

Subject will be instructed to not intentionally disturb the gauged struts, and how the subject can call the research team with any issues or concerns. The subject will be shown how the black protective mesh fits over the strut and how it may be repositioned properly in the event it is malpositioned.

The research team will schedule measurement sessions with the goal of conducting force measurements at approximately five different time points across the external fixator treatment, which can last from months to as much as a year and a half.

Force measurements will be conducted as an add-on session to the patient's routine clinical visits. A wireless electronic module will be temporarily fastened to the patient's external fixator, and wires will be connected to the struts. Subjects will be asked to walk across a predetermined, approximately 50 meter, cleared, flat path within the clinic. Patients will be asked to use the same ambulation pattern and aide device (crutch, cane, etc.) as they had been using over the past week. A nurse and/or member of the research team will walk alongside the patient. The patient will be allowed to take a break from walking if he/she requests. External fixator forces+foot forces will be recorded on a computer during walking. After each measurement session, the wireless electronic module and wiring to the struts will be removed and the connectors recapped.

Force data measured from the external fixator will be analyzed statistically to determine if it can serve as a functional indicator of bone healing, providing valuable information to clinicians and patients.

The apparatus and method of using described herein is intended to measure forces within external fixator devices 40 used to stabilize bone fractures (scaffolds which connect directly to bone through the skin). These forces should provide a functional indication of fracture healing, or early indication of progression of the patient toward poor healing. For example, use of Ilizarov external fixation may be utilized to stabilize a fractured tibia. In treating a fractured tibia, the fixators 40 may be kept on the patient for months or even more than a year, at significant inconvenience and risk of infection to the patient. The modified fixator 40 described above may be used to measure the forces in external fixator devices 40 that are used to stabilize bone fractures and inform the surgeon when to remove the fixator 40 base on the healing status of the bone. This technology could be a foundation for mobile monitoring of more ubiquitous fracture fixation implants and braces. The strut 10 designs may be modified based on principles of load cell design with the aim of amplifying/conditioning strains for more sensitive monitoring.

For example, the circular Ilizarov external fixator 40 may be used to treat a tibial fracture or defect. To measure the progress of healing at the fracture site, small strain gauges 20 may be adhered to vertical steel struts 10 which span the fracture site. The force measurements from these gauges 20 can provide an indication of functional bone healing.

A similar approach may be utilized with other medical braces and devices wherein similar instruments may be added to the braces and/or device to collect mechanical data from. As methodologies for interpreting this large volume of data continue to evolve, the data may be utilized to optimize the personalized treatment of individual patients. While an external fixator 40 is described in detail, it should be understood that the same principals, technologies, methodologies, and instruments may be applied to other braces and orthopedic devices.

An Ilizarov-type frame 40 modified with two instrumented struts 10 was installed by the Co-PI onto a tubular bone substitute, and a 2 cm segmental defect was created in the bone. Controlled forces up to 125 lbs. were applied along the axis of the 'bone', and forces were measured in the two struts 10 using the wireless transmitter 30 as described herein. The measured forces were very linear with applied load, and reproducible upon reloading. This testing also indicated that certain struts 10 will carry more load than others depending on the configuration of the frame 40. Additionally running computer simulations with finite element models to better understand the load transfer through the various struts 10 may improve the accuracy of predicting the bone healing status.

When the limb is mechanically loaded during standing and walking, the load is transmitted down through the struts 10 of the fixator 40, offloading the bone defect site. As healing progresses, the bone assumes a larger and larger share of the load, and the external fixator 40 should experience less load. This provides the potential opportunity to use sensors 20 on the external fixator 40 to develop potential indicators of functional fracture healing, which would be helpful to patients and clinicians. As part of routine standard care the patient will initially have placement of a standard circular external fixator 40 in a standard operation. This fixator 40 will not be instrumented at the time of the surgery. Statistical methods will be used to relate forces measured from circular external fixators 40 to bone healing, and develop potentially predictive methods (that could be formally validated in a larger study).

Figure 6:
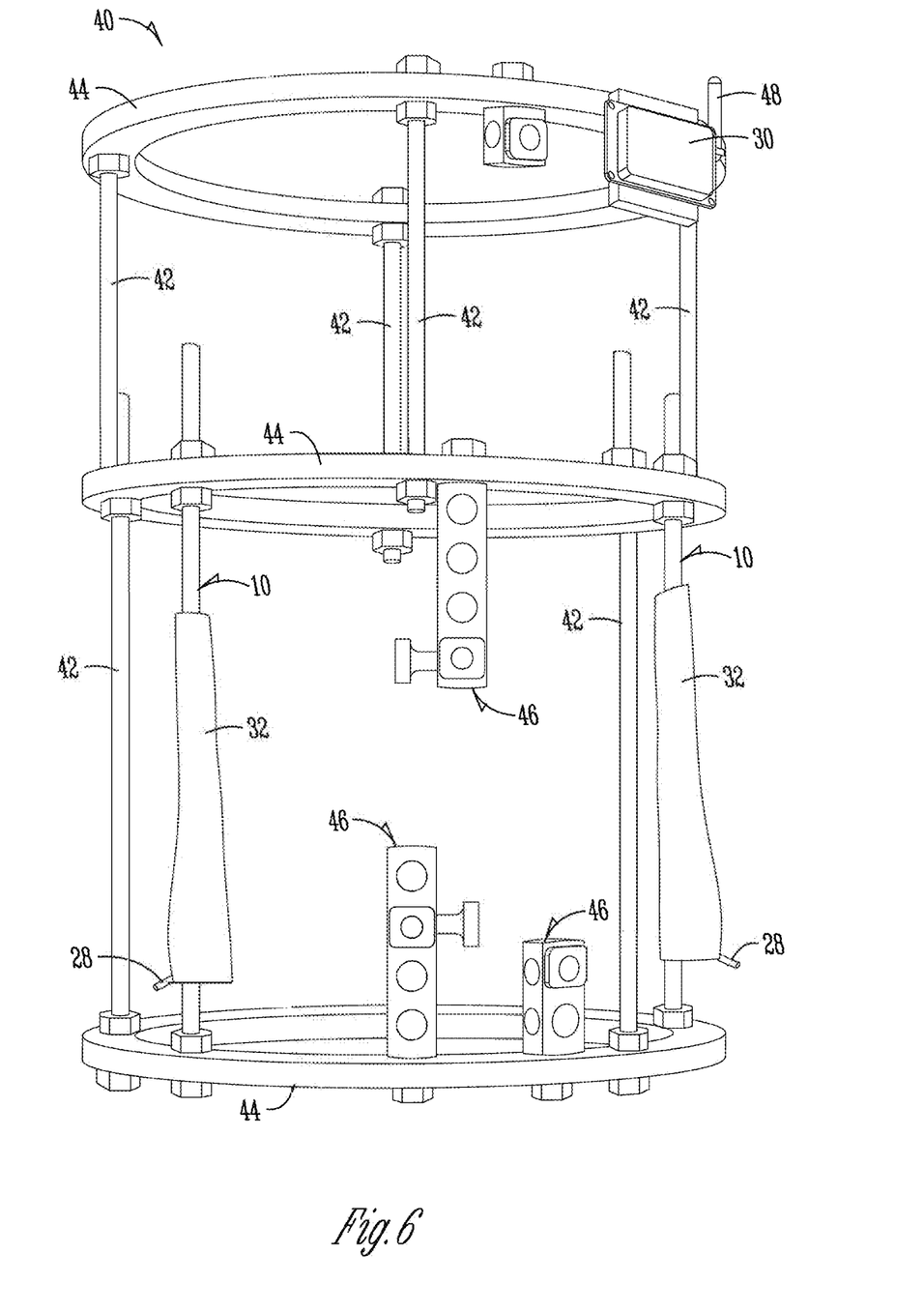
FIG. 6 is an example embodiment of an external fixator apparatus.

The standard fixator 40 includes vertical struts 42 which are fully-threaded 6 mm diameter (M6) 303 stainless steel rods or rods with similar mechanical characteristics. At a post-operative clinical visit, up to four of these struts 42 will be replaced by instrumented struts 10, as shown in FIG. 6. The instrumented struts 10 may be physically prepared and calibrated prior to being attached to the patient's fixator 40. The strut modification is designed to not impact normal clinical care and result in long term, accurate reliable force measurement. Furthermore, the strain gauges may be modified to fit a particular application and allow for improved installation and protection of the gauges on the strut 10. For example, the gauge 20 may be modified to fit a different support member of a different frame, brace, or orthopedic device. The gauge may also be modified to be attached to be attached to different textured surfaces and different profiled surfaces. For example, modified to be attached to a square or rectangular shaped strut or bar that has a rough or course surface.

Gauged struts 10 are similar to the normal 6 mm dia. threaded struts but include a central smooth region 14 of 6 mm diameter, as shown in FIGS. 1 and 2. Strain gauges 20 are adhered to the central smooth region 14 and protected from water and impact by a special coating(s) 22 and 24; a small waterproof connector 28 is wired (with coated wiring) to the gauge and fastened to the strut 10, and capped 34 while not in use. The gauges 20 and connector 28 are protected by a removable mesh 32.

The circular external fixator 40 to be used will be a modification of a normal fixator. The modification includes a small change in the vertical steel struts 42 and 10 to accommodate measurement of force. Struts 10 may be machined using documented machining and quality control protocols, and by experienced machinist with documented qualifications. Review of the protocol will be conducted, and inspection and measurements of the final parts completed by a research engineer. Other modifications may include adding protective coatings and wiring to the strut(s) 10. The vertical struts 10 are components that are entirely outside the patient's skin and thus any risk is expected to be minimal.

Prior to installation, the gauged struts 10 may be sterilized externally with ethanol and UV light and sealed in a sterile bag until installation on the fixator 40.

Figure 4:
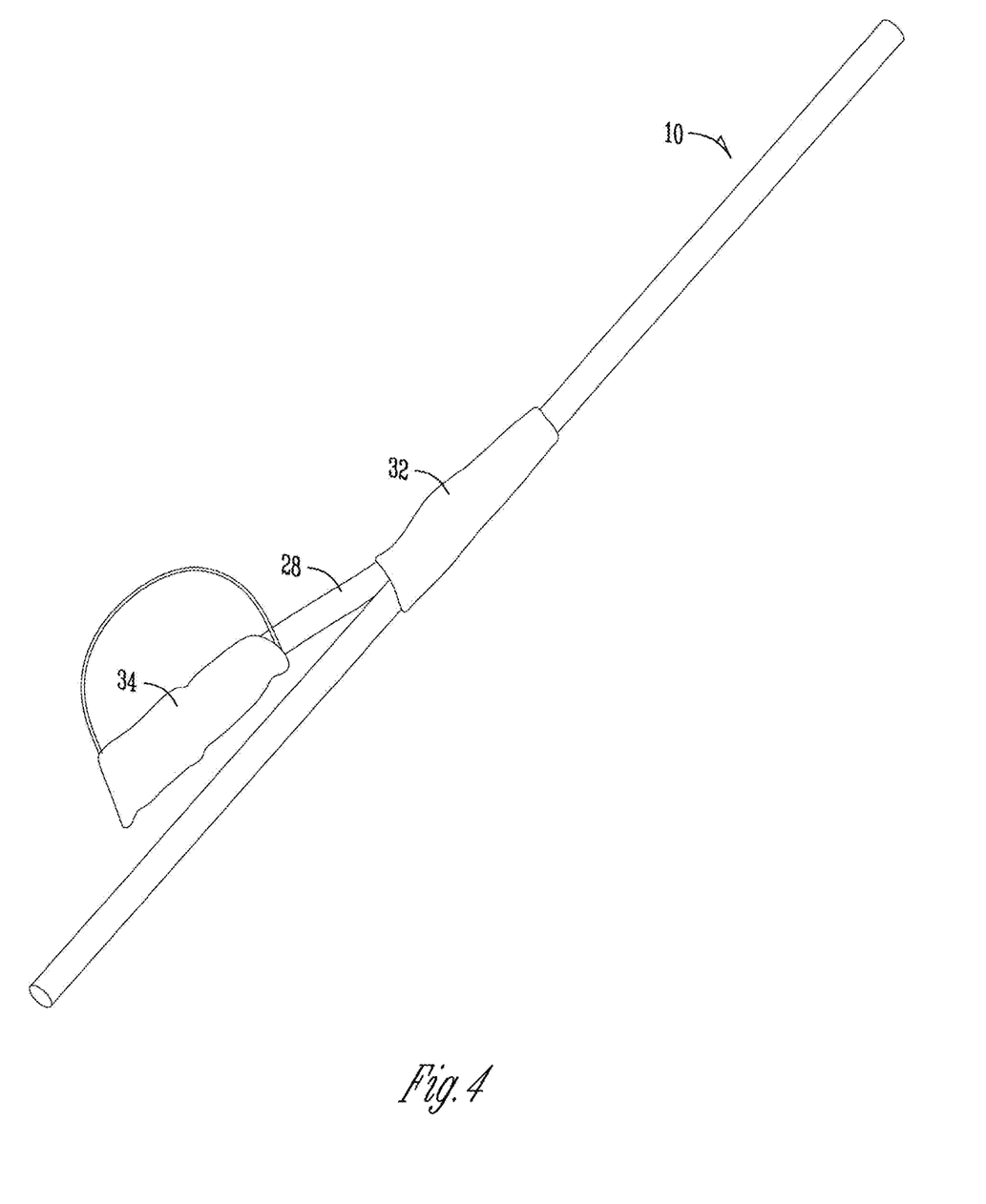
FIG. 4 is an example embodiment of a strut for an external fixator apparatus.
Figure 5:
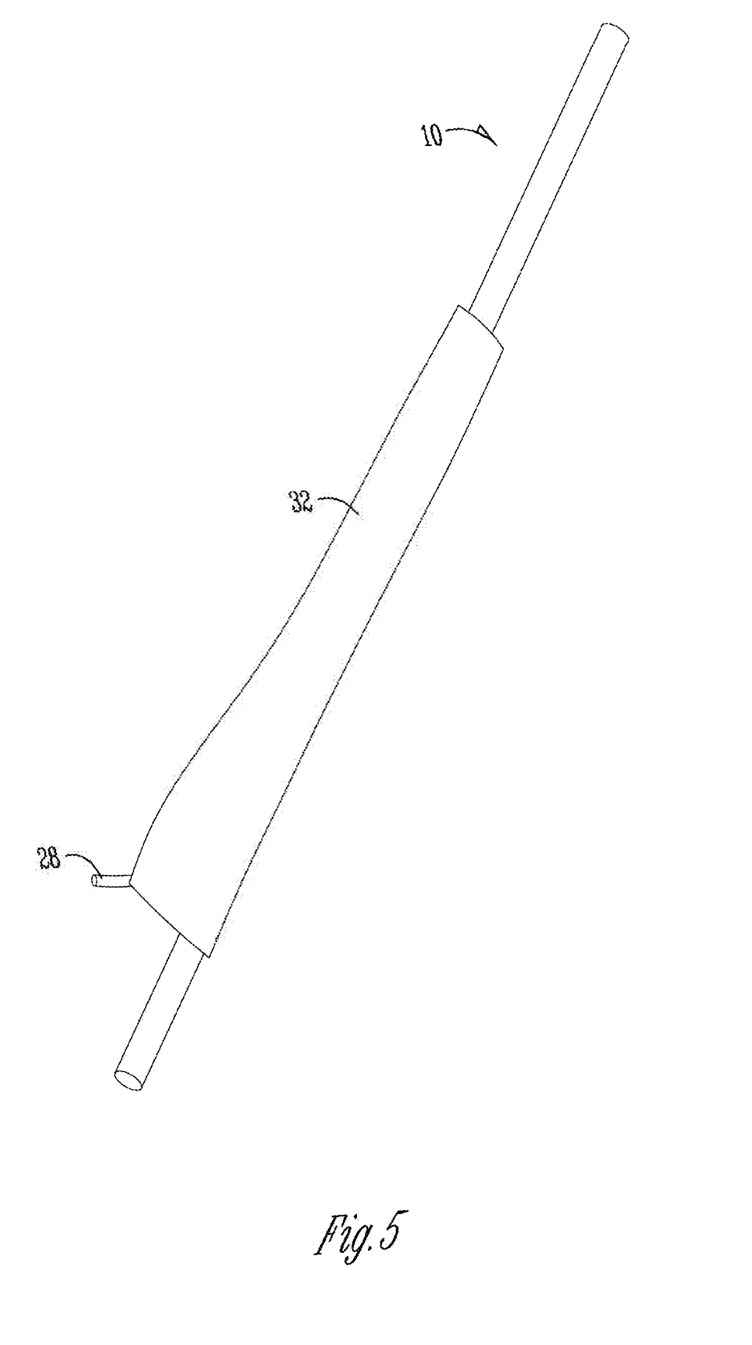
FIG. 5 is an alternative example embodiment of a strut for an external fixator apparatus including a flexible sleeve member covering the strut.

Strain gauges 20 are basically small passive wire resistors with an insulating backing. Active electronics 30 which excite the gauges with small voltages (<5V) may be removably wired to the gauges 20 when measurement are recorded, and removed when not needed. The electric connector 28 that is attached to the gauges 20 may be capped 34 when the active electronic 30 is not connected, as shown in FIG. 4.

Measurements made for this study will occur in conjunction with routine post-op clinical visits. Measurements for each patient may be taken at an established time interval. For example, measurement may be taken at approximately five different time points, each being approximately two weeks apart. The measurements taken at each interval may then be compared in order to adequately characterize the course of healing. Alternatively, measurements may be taken in monthly time intervals during fracture healing. However there may be variations in the timing of measurements for several reasons: (1) The length of time the patient is treated with the external fixator 40 varies from months to more than a year; (2) some patients visit the clinic more frequently (e.g. every 2 weeks) for a period of time such as during bone transport for severe defects; and (3) Some patients are initially not weight-bearing on their limb, thus any force measurements would not have clear meaning.

During a measurement session, the gauged struts 10 described above will be switched out with the normal struts 42, one at a time. A temporary additional strut may be added to the frame 40 during the switching procedure to prevent any transient instability of the frame 40. Black protective mesh 32 fits over the strut 10 and may be repositioned properly in the event it is malpositioned.

Figure 7:
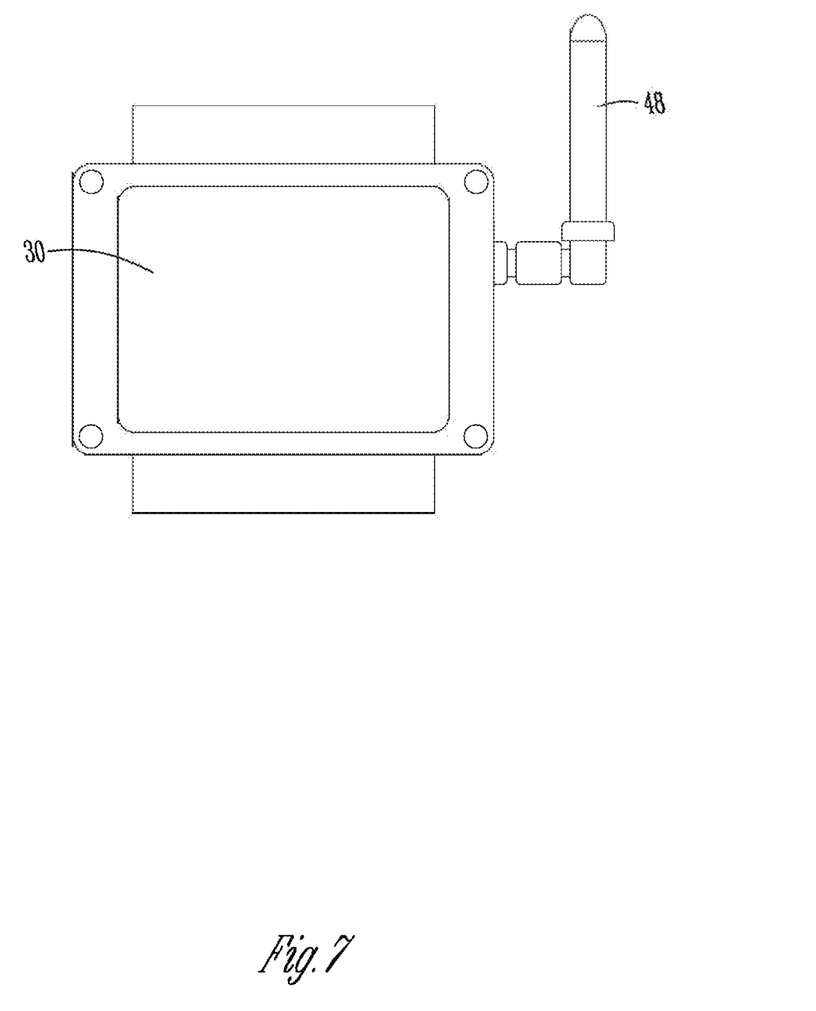
FIG. 7 is an example embodiment of an electronic module.

A wireless electronic module 30 (74 mm×79 mm×20 mm plus small antenna 48, weight ~150 grams, see figure below) (V-Link LXRS, Lord Microstrain) will be temporarily fastened to the patient's external fixator, and wires will be connected to the struts 10. This electronic module 30 will collect and transmit signals from the strain-gauged struts 10 on the fixator 40. A wireless router connected to a computer will collect the data.

In addition to the gauged struts 10, foot plantar force may be measured using portable instrumented shoe insoles. Because patients generally have varying amounts of weight-bearing on their injured limb, the data from the external fixators 40 may be normalized based on the measured foot plantar force. The insoles are available in different sizes. The appropriate sized insole may be inserted into the patient's own shoe(s). Insoles will be calibrated in a process that may use the patient's body weight. Data transmission is by wireless Bluetooth, from a small component also attached to the shoe.

Figure 8:
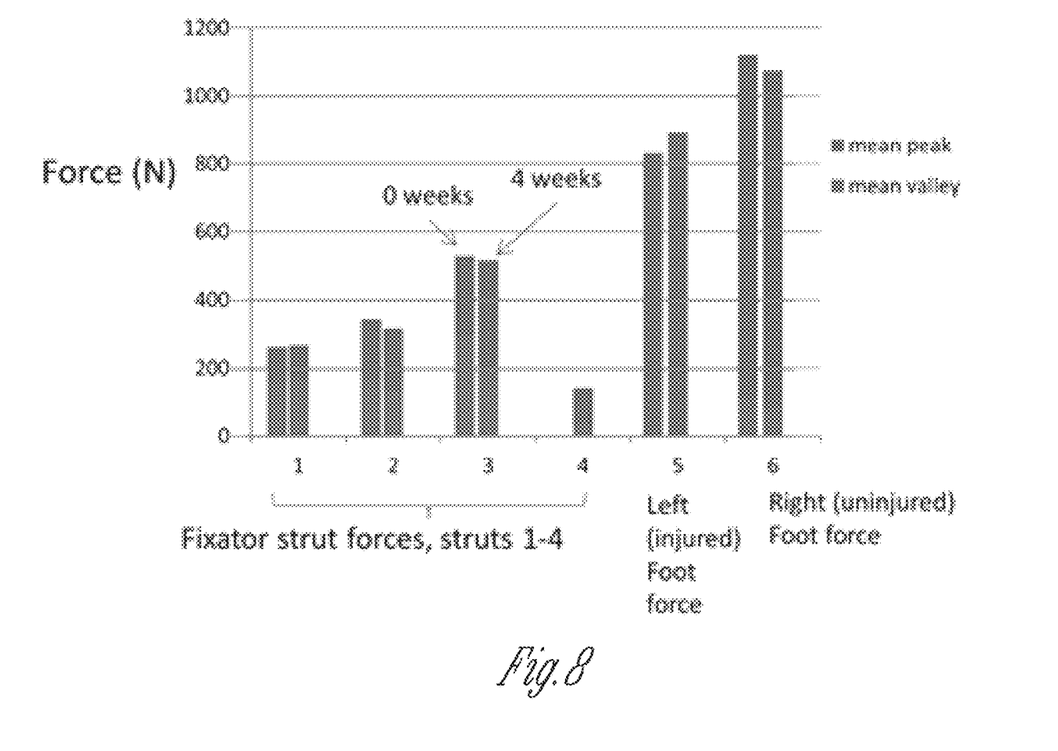
FIG. 8 shows a graph depicting mean peak and valley force levels during gait, patient.
Figure 9:
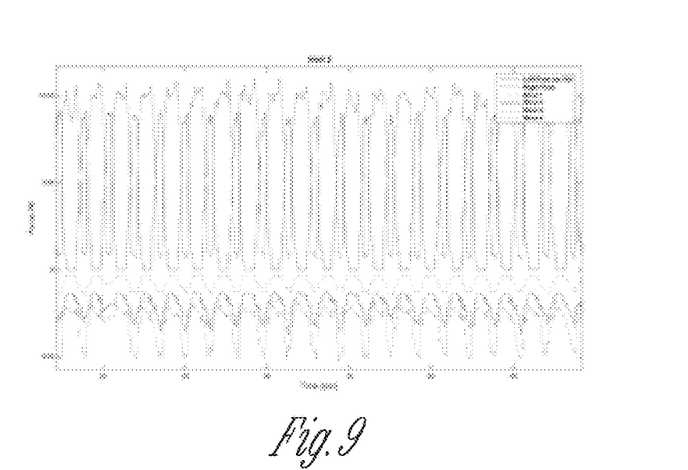
FIG. 9 shows part of original data curves for visit 2 and in particular repeatability across gait cycles in all force signals; peaks and valleys were obtained for all cycles (automatically using software) and averaged to obtain summary.

Subjects wearing the external fixator 40, including the modified strut(s) 10, and/or the shoe insole will be asked to walk across a predetermined, approximately 50 meters, along a cleared and flat path. The length of the walking course may be shortened as needed if the patient expresses concern over the proscribed 50 meter distance. Patients may be asked to use the same ambulation pattern and aide device (crutch, cane, etc.) as they had been using over the past week. External fixator forces and foot forces will be sampled during walking. Following measurements, the wireless electronic module 30 and associated wiring to the struts 10 will be removed from the patient's fixator 40 and the connector(s) 28 recapped 34. Also the foot insole devices will be removed from the patient's shoe(s). FIGS. 8 and 9 are two graphs showing sample of the data and measurements collected from a sample patient wearing the device(s) described above.

The disclosure is not to be limited to the particular embodiments described herein. The foregoing description has been presented for purposes of illustration and description. It is not intended to be an exhaustive list or limit any of the disclosure to the precise forms disclosed. It is contemplated that other alternatives or exemplary aspects of the present invention are understood to be considered included in the disclosure. The description(s) provided above are merely examples of embodiments, processes or methods of the disclosure. It is understood that any other modifications, substitutions, and/or additions can be made, which are within the intended spirit and scope of the disclosure. For the foregoing, it can be seen that the disclosure accomplishes at least all that is intended.

The previous detailed description is of a small number of embodiments for implementing the disclosure and is not intended to be limiting in scope. The following claims set forth a number of the embodiments of the disclosure with greater particularity.

REFERENCES

1. Dendrinos, G. K., Kontos, S. & Lyritsis, E. Use of the Ilizarov technique for treatment of non-union of the tibia associated with infection. *J. Bone Joint Surg. Am.* 77, 835-846 (1995).
2. National Center for Health Statistics National Health Interview Survey. (2005).
3. Cierny, G., 3rd & Zorn, K. E. Segmental tibial defects. Comparing conventional and Ilizarov methodologies. *Clin. Orthop.* 118-123 (1994).
4. Keeling, J. J., Gwinn, D. E., Tintle, S. M., Andersen, R. C. & McGuigan, F. X. Short-Term Outcomes of Severe Open Wartime Tibial Fractures Treated with Ring External Fixation. *J. Bone Jt. Surg.* 90, 2643-2651 (2008).
5. Ilizarov, G. A. The principles of the Ilizarov method. *Bull. Hosp. Jt. Dis. Orthop. Inst.* 48, 1-11 (1988).
6. Gessmann, J., Jettkant, B., Schildhauer, T. A. & Seybold, D. Mechanical stress on tensioned wires at direct and indirect loading: A biomechanical study on the Ilizarov external fixator. *Injury* 42, 1107-1111 (2011).
7. D'Lima, D. D., Fregly, B. J. & Colwell, C. W. Implantable sensor technology: measuring bone and joint biomechanics of daily life in vivo. *Arthritis Res. Ther.* 15, 203 (2013).
8. Aronson, J. Limb-lengthening, skeletal reconstruction, and bone transport with the Ilizarov method. *J. Bone Joint Surg. Am.* 79, 1243-1258 (1997).
9. Catagni, M. A., Guerreschi, F. & Lovisetti, L. Distraction osteogenesis for bone repair in the 21st century: lessons learned. *Injury* 42, 580-586 (2011).
10. Richardson, J. B., Cunningham, J. L., Goodship, A. E., O'Connor, B. T. & Kenwright, J. Measuring stiffness can define healing of tibial fractures. *J. Bone Joint Surg. Br.* 76-B, 389-394 (1994).
11. Burny, F., Burny, W., Donkerwolcke, M. & Behrens, M. Effect of callus development on the deformation of external fixation frames. *Int. Orthop.* 36, 2577-2580 (2012).
12. Windhagen, H., Bail, H., Schmeling, A., Kolbeck, S., Weiler, A. & Raschke, M. A new device to quantify regenerate torsional stiffness in distraction osteogenesis. *Biomech.* 32, 857-860 (1999).
13. Aronson, J. & Harp, J. H. Mechanical forces as predictors of healing during tibial lengthening by distraction osteogenesis. *Clin. Orthop.* 73-79 (1994).
14. Floerkemeier, T., Hurschler, C., Witte, F., Wellmann, M., Thorey, F., Vogt, U. & Windhagen, H. Comparison of various types of stiffness as predictors of the load-bearing capacity of callus tissue. *J. Bone Joint Surg. Br.* 87, 1694-1699 (2005).
15. Grasa, J., Gómez-Benito, M. J., González-Torres, L. A., Asiaín, D., Quero, F. & García-Aznar, J. M. Monitoring In Vivo Load Transmission Through an External Fixator. *Ann. Biomed. Eng.* 38, 605-612 (2010).
16. Windhagen, H., Kolbeck, S., Bail, H., Schmeling, A. & Raschke, M. Quantitative assessment of in vivo bone regeneration consolidation in distraction osteogenesis. *J. Orthop. Res. Off. Publ. Orthop. Res. Soc.* 18, 912-919 (2000).
17. Aarnes, G. T., Steen, H., Ludvigsen, P., Waanders, N. A., Huiskes, R. & Goldstein, S. A. In vivo assessment of regenerate axial stiffness in distraction osteogenesis. *J. Orthop. Res. Off. Publ. Orthop. Res. Soc.* 23, 494-498 (2005).
18. Kirane, Y. M., Lewis, G. S., Sharkey, N. A. & Armstrong, A. D. Mechanical characteristics of a novel posterior-step prosthesis for biconcave glenoid defects. *J. Shoulder Elbow Surg.* 21, 105-115 (2012).
19. Whelan, D. B., Bhandari, M., McKee, M. D., Guyatt, G. H., Kreder, H. J., Stephen, D. & Schemitsch, E. H. Interobserver and intraobserver variation in the assessment of the healing of tibial fractures after intramedullary fixation. *J. Bone Joint Surg. Br.* 84, 15-18 (2002).

What is claimed is:

1. An external fixator medical apparatus, the apparatus comprising:
   a frame including one or more ring members;
   a plurality of strut members interconnecting the one or more ring members;
   one or more strut gauges attached, by an epoxy, to a smooth central portion of at least one of the plurality of strut members, said one or more strut gauges configured to measure the strains acting on the at least one of the plurality of strut members; and
   an acrylic coating covering the epoxy so as to create a water tight seal;
   wherein the acrylic coating is further protected by a silicone coating; and
   further wherein a polyester mesh sleeve wholly covers a circumference of the at least one of the plurality of strut members.

2. The apparatus of claim 1, further comprising bone support members extending from the one or more ring members, said bone support members configured to contact and support a fractured bone.

3. The apparatus of claim 1, wherein the one or more strut gauges are strain gauges, and wherein the mechanical forces acting on the strut are calculated based on the strains measured by the strain gauges.

4. The apparatus of claim 1, wherein the plurality of strut members are made of 303 stainless steel that meets ASTM A582.

5. The apparatus of claim 1, further comprising an electronic module that may be attached to the frame and connected to the one or more gauges, said electronic module configured to collect and transmit signals from the one or more gauges.

6. The apparatus of claim 5, wherein the electronic module is configured to wirelessly transmit data collected from the one or more gauges to a computer.

7. The apparatus of claim 1, wherein the smooth central section comprises a diameter of 6 millimeters.

8. The apparatus of claim 7, wherein the plurality of strut members comprise opposing threaded end portions, said threaded end portions comprising M6×1 threads.

9. The apparatus of claim 1, further comprising an electrical connector extending from the one or more strut gauges.

* * * * *